United States Patent
Hu et al.

(10) Patent No.: US 11,238,989 B2
(45) Date of Patent: Feb. 1, 2022

(54) PERSONALIZED RISK PREDICTION BASED ON INTRINSIC AND EXTRINSIC FACTORS

(71) Applicant: International Business Machines Corporation, Armonk, NY (US)

(72) Inventors: Gang Hu, Beijing (CN); Xiang Li, Beijing (CN); Hai Feng Liu, Beijing (CN); Jing Mei, Beijing (CN); Eryu Xia, Beijing (CN); En Liang Xu, Beijing (CN); Shi Wan Zhao, Beijing (CN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 783 days.

(21) Appl. No.: 15/806,757

(22) Filed: Nov. 8, 2017

(65) Prior Publication Data

US 2019/0138691 A1 May 9, 2019

(51) Int. Cl.
*G16H 50/30* (2018.01)
*G06N 7/00* (2006.01)
*G06N 20/00* (2019.01)
*G16H 50/20* (2018.01)
*G16H 50/70* (2018.01)

(52) U.S. Cl.
CPC ............. *G16H 50/30* (2018.01); *G06N 7/005* (2013.01); *G06N 20/00* (2019.01); *G16H 50/20* (2018.01); *G16H 50/70* (2018.01)

(58) Field of Classification Search
CPC combination set(s) only.
See application file for complete search history.

(56) References Cited

U.S. PATENT DOCUMENTS

| | | |
|---|---|---|
| 2008/0172214 A1* | 7/2008 | Col et al. |
| 2010/0204920 A1 | 8/2010 | Dranitsaris et al. |
| 2011/0066454 A1 | 3/2011 | Rosauer et al. |
| 2015/0220698 A1* | 8/2015 | Argyropoulos et al. |
| 2016/0180050 A1 | 6/2016 | Holmes et al. |
| 2016/0283686 A1 | 9/2016 | Hu et al. |
| 2017/0277841 A1* | 9/2017 | Shankar et al. |
| 2018/0082172 A1* | 3/2018 | Patel et al. |

(Continued)

OTHER PUBLICATIONS

Lan, et al., "Disease Risk Prediction by Mining Personalized Health Trend Patterns: A Case Study on Diabetes," 2012 Conference on Technologies and Applications of Artificial Intelligence, 6 pages.

*Primary Examiner* — Michael Tomaszewski
*Assistant Examiner* — William T. Monticello
(74) *Attorney, Agent, or Firm* — Amin, Turocy & Watson, LLP

(57) ABSTRACT

Systems, computer-implemented methods and/or computer program products that facilitate predicting personalized risks based on intrinsic factors and extrinsic factors are provided. In one example, a computer-implemented method comprises: collecting, by a system operatively coupled to a processor, intrinsic factors and extrinsic factors associated with infectious diseases; generating, by the system, a probabilistic model based on the intrinsic factors and extrinsic factors, wherein the model incorporates node characteristics into infection probability; and refining, by the system, the model through concurrently learning respective node thresholds and hidden infection network structure of the model.

20 Claims, 13 Drawing Sheets

(56) References Cited

U.S. PATENT DOCUMENTS

2018/0349548 A1\* 6/2018 Walsh et al.
2018/0226153 A1\* 8/2018 Rubenstein et al.
2018/0366221 A1\* 12/2018 Crehore et al.
2019/0172587 A1\* 6/2019 Park et al.

\* cited by examiner

PERSONALIZED RISK PREDICTION BASED ON INTRINSIC AND EXTRINSIC FACTORS

BACKGROUND

The subject disclosure relates to facilitating predicting personalized risks, and more specifically, providing risk prediction based on intrinsic factors and extrinsic factors.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments herein, devices, systems, computer-implemented methods, apparatus and/or computer program products that facilitate predicting personalized risks based on intrinsic factors and extrinsic factors.

According to one embodiment, a system is provided. The system can comprise a memory that stores computer executable components. The system can also comprise a processor, operably coupled to the memory, and that can execute computer executable components stored in the memory. The computer executable components can comprise a collection component that can collect intrinsic factors and extrinsic factors associated with infectious diseases. The computer executable components can further comprise a construction component that can generate a probabilistic model based on the intrinsic factors and extrinsic factors, wherein the probabilistic model incorporates node characteristics into infection probability. The computer executable components can further comprise a machine learning component that can refine the probabilistic model through concurrently learning respective node thresholds and hidden infection network structure of the probabilistic model.

According to another embodiment, a computer-implemented method is provided. The computer-implemented method can comprise collecting, by a system operatively coupled to a processor, intrinsic factors and extrinsic factors associated with infectious diseases. The computer-implemented method can further comprise generating, by the system, a probabilistic model based on the intrinsic factors and extrinsic factors, wherein the probabilistic model incorporates node characteristics into infection probability. The computer-implemented method can further comprise refining, by the system, the probabilistic model through concurrently learning respective node thresholds and hidden infection network structure of the probabilistic model.

According to another embodiment, a computer program product that facilitates predicting personalized risks based on intrinsic factors and extrinsic factors is provided. The computer program product can comprise a computer readable storage medium having program instructions embodied therewith. The program instructions can be executable by a processor to cause the processor to collect intrinsic factors and extrinsic factors associated with infectious diseases. The program instructions can further be executable by a processor to cause the processor to generate a probabilistic model based on the intrinsic factors and extrinsic factors, wherein the probabilistic model incorporates node characteristics into infection probability. The program instructions can further be executable by a processor to cause the processor to refine the probabilistic model through concurrently learning respective node thresholds and hidden infection network structure of the probabilistic model.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

One or more embodiments described herein can facilitate predicting personalized risks (e.g., risk prediction) based on intrinsic factors and extrinsic factors. The personalized risk or risk prediction can predict the susceptibility (or likelihood) of a person contracting an infectious disease. Intrinsic factors (e.g., intrinsic risks) denote the threshold or susceptibility of a person, which could be a complicated function of the person's intrinsic characteristics (e.g., age, weight, height, etc.). Extrinsic factors (e.g., extrinsic risks) denote the influence of others through user interaction (e.g., time of infection, interactions with infected persons, property of infectious diseases, influence of others, etc.). In one or more embodiments, the intrinsic risk can be calculated based on the patient characteristics. The extrinsic risk can be calculated based on the interactions between the patients. In some embodiments, the personalized risk models (e.g., risk prediction models, probabilistic models, models, etc.) can be generated by fusing together the intrinsic risk and the extrinsic risk. The risk prediction models can be used in clinical decision making to help patients make informed choices about their treatments. For example, the risk prediction models can predict the likelihood that a patient will be infected after an exposure to an infection. This allows the patient to weigh between the benefits of getting a treatment for a possible infection and the side effects of receiving the treatment.

Figure 1:
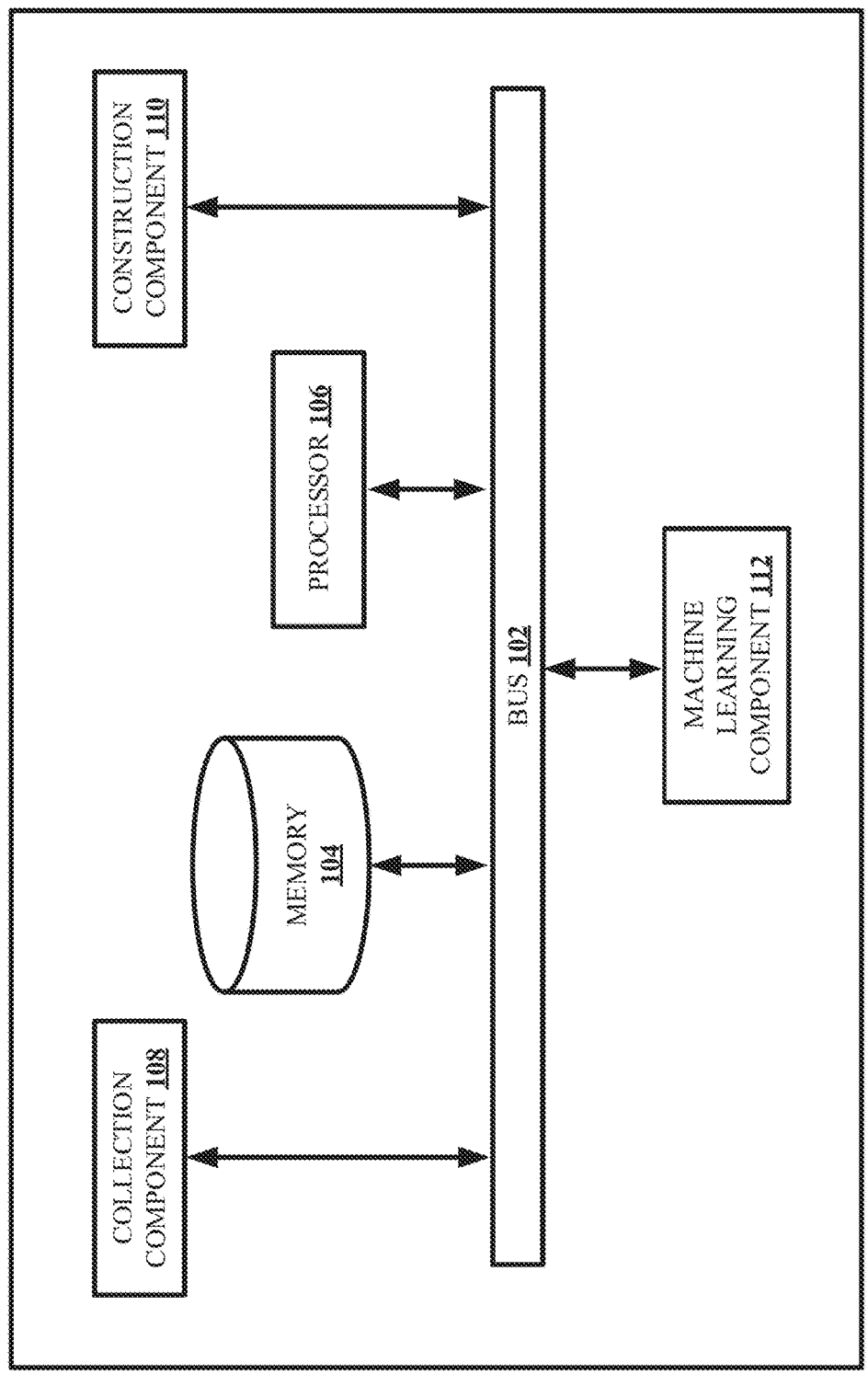
FIG. 1 illustrates a block diagram of an example, non-limiting system facilitating predicting personalized risks based on intrinsic factors and extrinsic factors in accordance with one or more embodiments described herein.

FIG. 1 illustrates a block diagram of an example, non-limiting system 100 facilitating predicting personalized risks based on intrinsic factors and extrinsic factors in accordance with one or more embodiments described herein. Aspects of systems (e.g., system 100 and the like), apparatuses or processes explained in this disclosure can constitute one or more machine-executable components embodied within one or more machines, e.g., embodied in one or more computer readable mediums (or media) associated with one or more machines. Such components, when executed by the one or more machines, e.g., computers, computing devices, virtual machines, etc., can cause the machines to perform the operations described.

In various embodiments, the system 100 can be any type of component, machine, device, facility, apparatus, and/or instrument that comprises a processor. In some embodiments, system 100 is capable of effective and/or operative communication with a wired and/or wireless network. Components, machines, apparatuses, devices, facilities, and/or instrumentalities that can comprise the system 100 can include, but are not limited to, tablet computing devices, handheld devices, server class computing machines and/or databases, laptop computers, notebook computers, desktop computers, cell phones, smart phones, consumer appliances and/or instrumentation, industrial and/or commercial devices, digital assistants, multimedia Internet enabled phones, multimedia players, and the like.

As illustrated in FIG. 1, the system 100 can comprise bus 102, memory 104, processor 106, collection component 108, construction component 110 and/or machine learning component 112. The bus 102 can provide for interconnection of various components of the system 100. The memory 104 and processor 106 can carry out computation and/or storage operations of the system 100 as described herein. It is to be appreciated that in some embodiments one or more system components can communicate wirelessly with other components, through a direct wired connection or integrated on a chipset.

In one or more embodiments described herein, the system 100 can employ predictive analytics to automatically generate a probabilistic model (e.g., a risk prediction model, etc.). For example, the automatic generation can be based on information retained in a knowledge base. As used herein, the term "knowledge base" can be a database or other storage location or repository that can store one or more types of information. All such embodiments are envisaged.

The knowledge base can comprise information related to one or more intrinsic factors and one or more extrinsic factors. The intrinsic factors can be used to determine the threshold or susceptibility of a person. The threshold or susceptibility of a person can be a function of the person's characteristics such as age, weight, height, etc. The extrinsic factors can signify the influence of others through interactions. The extrinsic factors can be the time of infection, time of interaction with an infected person, etc. In some embodiments, the information related to the one or more intrinsic factors and the one or more extrinsic factors can be gathered over time and retained in the knowledge base. In some embodiments, the information gathered can include age, weight, height, time of infection, etc.

Based on the obtained information, the system 100 can evaluate the knowledge base (or multiple knowledge bases) and generate one or more patterns and/or can map information known about a patient to the information known about other patients. The evaluation is based on whether the data points (e.g., intrinsic factors and extrinsic factors) is similar to the probabilistic models generated by the machine learning component 112. The predictive analytics of the system 100 (e.g., the machine learning component 112) can determine that, if information associated with a patient is similar to one or more other patients, the relationships among the patients can be utilized to automatically generate the risk prediction models. The similarity can be determined based on whether the data for a patient matches with a model. For example, if a patient has the same type of characteristics (e.g., intrinsic factors) and interactions (e.g., extrinsic factors) as a probabilistic model, the probabilistic model can be used to generate risk predictions for the patient.

The computer processing systems, computer-implemented methods, apparatus and/or computer program products described herein can employ hardware and/or software to generate probabilistic models that are highly technical in nature, that are not abstract and that cannot be performed as a set of mental acts by a human. For example, the construction component 110 can generate models based on hundreds of pieces of data (e.g., intrinsic factors and extrinsic factors). In another example, one or more embodiments can determine and/or analyze the infection probability to determine the probability of infection from one node to another node (e.g., one person to another person). In yet another example, one or more embodiments can determine and/or analyze risk prediction to predict personalized risk. Furthermore, the one or more embodiments can perform the lengthy interpretation and analysis on the available information to determine node threshold and network structure simultaneously or concurrently. The node threshold can be determined based on hundreds of intrinsic factors or characteristics of a person. The network structure or the infection network structure can be determined based on hundreds of interactions that a person can have. In another example, the one or more embodiments can perform predictive analytics on a large amount of data to automatically facilitate generating a probabilistic model based on the intrinsic factors and extrinsic factors. The probabilistic model can be built using nodes. The nodes (e.g., representing a person) can include node features, which can be intrinsic factors and extrinsic factors that can affect the node's (e.g., the person's) susceptibility of contracting an infection. The intrinsic factors can be characteristics of a person such as age, weight, height, etc. The intrinsic factors of a node (e.g., a person) can be used to determine the node's threshold. The extrinsic factors (e.g., time of infection, influence of others, etc.) can be used to determine the value of the active neighbors (e.g., the strength of an infection). The nodes in a probabilistic model can include node features such as the threshold and the value of the active neighbors. If the threshold is bigger than the value of the active neighbors then the node will likely not be susceptible to an infection. However, if the threshold is less than the value of the active neighbors, the node will likely be susceptible to an infection. Accuracy can be evaluated by comparing a training set with a test set. Links or arrows can also connect a node to another node to demonstrate interactions between the nodes. A probability of infection can be associated with the links to show the probability of one node infecting another node. The probability of infection can be determined based on the infection probability equation. After training a model employing a training set, accuracy can be calculated using a test set by computing percentage of output generated by the model running on the training set elements that matches a predicted target.

The collection component 108 can collect the intrinsic factors and the extrinsic factors associated with infectious diseases. The intrinsic factors can be characteristics about a person (e.g., a patient) that can help a person fight off an infection (e.g., tolerance or immunity or lack thereof). The intrinsic factors can be characteristics such as age, weight, height, etc. For example, a person's age can have a significance as to whether that person will contract an infection. For example, youngsters and senior people can have weaker immune systems and can be more prone to infections than young adults.

The characteristics describing a person's intrinsic factors can be incorporated (e.g., via the construction component 110) into the nodes as node characteristics. A node is representative of a patient or person. The links between the nodes can represent the interactions or the infection probability between the nodes. A patient or person can provide data for the intrinsic factors such as data rendered during an office exam, survey response, etc. The data can also come from other sources such as the patient's medical record, past medical history, family medical history, etc.

The extrinsic factors can be the time of infection, interaction with others, property of infectious diseases, influence of others, etc. The data for the extrinsic factors can be observed/detected and received by the system through the collection component 108 by any number of different types of entities including, but not limited to, a machine, hardware, software and/or a human. For example, students in school can be observed and the time of the infection can be recorded by an entity and input into the collection component 108. The observation can also be that an interaction did not result in the transferring of an infectious disease. The data for the extrinsic factors can also come from a database from a health agency that keep records of infectious disease outbreaks. For example, a government agency may have surveillance data for infectious diseases. The time of the infection can be used to solve the hidden infection network structure. Based on the threshold and infection probability of the nodes, the machine learning component 112 can learn the hidden infection network structure.

The construction component 110 can generate a probabilistic model based on the intrinsic factors and extrinsic factors. The construction component 110 can generate a probabilistic model by constructing the nodes with node features (e.g., intrinsic factors, extrinsic factors, thresholds and active neighbors). The probabilistic model can incorporate node characteristics that are intrinsic factors (e.g., age, weight, height, etc.) to determine the node threshold. The probabilistic model can incorporate extrinsic factors (e.g., time of infection, interaction, influence of others, etc.) to determine the value of the active neighbors. The probability of infection from one node to another node can be calculated using the infection probability equation. If the value of the threshold is higher than the value of the active neighbor (e.g., the strength of infection from a neighboring node), the node will likely not be infected. The opposite is true if the value of the threshold is less than the value of the active neighbor, and the node will likely become infected.

The nodes can be constructed to represent a person or patient. The connections between the nodes can be based on the connections or interactions between the patients or persons. The intrinsic factors (e.g., intrinsic characteristics of a person) can be incorporated into the nodes as node threshold. One person may have different intrinsic characteristics from another person, hence, a node that represents one person may have a different node threshold from a node that represents another person. For example, an adult can have a stronger immune system and so the node threshold representing the adult can be higher than the node threshold representing a youngster who has a weaker immune system.

The machine learning component 112 can refine the model through concurrently learning respective node thresholds and hidden infection network structure of the model. The node threshold can be used to determine the susceptibility of infection by the node. The hidden infection network structure can be used to determine the interactions or connections between the nodes. Based on the intrinsic factors collected by the collection component 108, the machine learning component 112 can learn the node thresholds. For example, the threshold of a node is a function of the node characteristics such as age, weight, height, etc. The time of infection and the interactions can be used to learn (e.g., via the machine learning component 112) the hidden infection network structure of the model. The infection network can generate information as to when the first person or the first group of individuals became infected and when that infection transmitted to the next group and so on. The machine learning component 112 can also calculate intrinsic risks and extrinsic risks based on individual characteristics and interactions. The intrinsic risk and the extrinsic can be determined from the risk prediction equation. The machine learning component 112 can also calculate personalized risks (e.g., risk prediction for the patients, persons, etc.) as a function of the intrinsic risks (e.g., age, weight, height, etc.) and the extrinsic risks (e.g., time of infection, interaction, influence of others, etc.). The personalized risks can be determined by calculating the risk prediction equation.

The risk of a node (e.g., personalized risk) is a function of the intrinsic risk and the extrinsic risk. The risk of a node can be represented by the risk prediction equation $F(x)=\pi*LR(x)+(1-\pi)*NW(x)$. The risk prediction equation can be calculated by the machine learning component 112. The expression $F(x)$ is the personalized risk of node x. The symbol $\pi$ is a parameter that can be set to control the importance of intrinsic risk $LR(x)$ and extrinsic risk $(NW(x))$. The expression $LR(x)$ can be used to represent the intrinsic risk of node x. The expression $LR(x)$ can also be determined from calculating $(1-Threshold(x))$. The expression $Threshold(x)$ is the threshold of node x, which can be a function of characteristics (e.g., age, weight, height, etc.) of node x. The intrinsic risk can be calculated from the intrinsic factors that characterizes a person such as age, weight, height, etc. The intrinsic risk ($LR(x)$) can be a Linear Regression function, Cox function or some other functions of the node characteristics (e.g., age, weight, height, etc.). The expression $NW(x)$ can be used to represent the extrinsic risk. The extrinsic risk can be calculated from the extrinsic factors such as the time a person received an infection, the interactions a person has with others, etc. Each node can be infected by its neighbors with probability $$Pc(x, y) = (1 - \text{Threshold}(x)) * e^{-\frac{\Delta}{\alpha}} * (1 - \text{Threshold}(y)).$$

(See the infection probability equation below.) The extrinsic risk (NW(x)) can be the sum or some other functions of these probabilities. The property of an infectious disease can also be factored in to calculate the infection probability as extrinsic risk. A parameter representing the property of infectious disease can be added along with a coefficient for the extrinsic risk (NW(x)).

The expression F(x) can be used to represent personalized risk of a node (e.g., a person). The personalized risk or F(x) can be calculated (e.g., via the machine learning component 112) to describe the risk prediction of a node (e.g., a person) based on individual characteristics (e.g., intrinsic factors) and interactions (e.g., extrinsic factors). The risk prediction or personalized risk can determine the susceptibility of a person for contracting an infectious disease.

Figure 2:
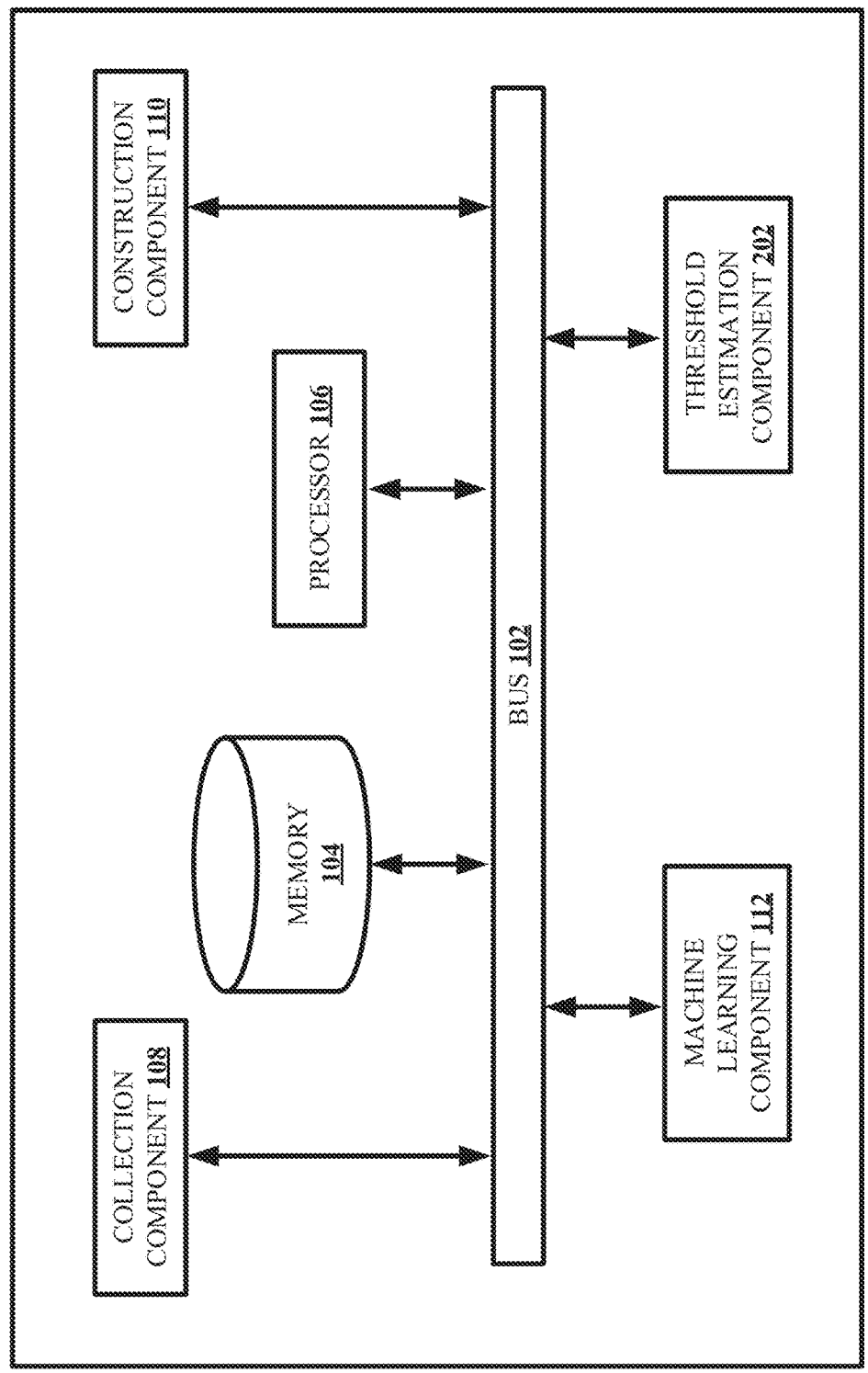
FIG. 2 illustrates a block diagram of an example, non-limiting system facilitating predicting personalized risks based on intrinsic factors and extrinsic factors including a threshold estimation component in accordance with one or more embodiments described herein.

FIG. 2 illustrates a block diagram of an example, non-limiting system 200 facilitating predicting personalized risks based on intrinsic factors and extrinsic factors including a threshold estimation component 202 in accordance with one or more embodiments described herein. Repetitive description of like elements employed in other embodiments described herein is omitted for sake of brevity.

The threshold estimation component 202 can estimate the thresholds of the nodes within the models. The thresholds of the nodes can be estimated or calculated using the node characteristics. The threshold is a function of node characteristics (e.g., age, weight, height, etc.). The threshold can be a simple linear function or some complex functions. As an example, for the linear function, Threshold(x)=w0+w1*age+w2*weight+ . . . . The variables w0, w1, w2 . . . are coefficients, which can be learned. The thresholds of a nodes are a function of age, weight, height, etc. The threshold of the node can be used to determine the infection probability of the node using the infection probability equation. The higher the threshold of a node (e.g., a person), the less susceptible the node is to infections. The threshold estimation component 202 can also calculate the infection probability based on the thresholds using the infection probability equation.

The property of a disease can be represented by the infection probability equation $$Pc(x, y) = (1 - Threshold(x)) * e^{-\frac{\Delta}{\alpha}} * (1 - Threshold(y)).$$

The infection probability equation calculates the probability of node x infecting node y. Initially, a node has a random threshold in [0,1]. The node thresholds can be learned in model learning by calculating the maximum likelihood estimation of the probabilistic model. A node can be infected by its neighbors with probability $$Pc(x, y) = (1 - Threshold(x)) * e^{-\frac{\Delta}{\alpha}} * (1 - Threshold(y)).$$

The value of the "active neighbors" is the sum of these probabilities. If the value of the active neighbors is bigger than the threshold, the node will become active.

The Threshold(x) is the threshold of node x. The Threshold(y) is the threshold of node y. The expression $$Pc(x, y) = f(x) * e^{-\frac{\Delta}{\alpha}} * f(y).$$

is an exponential model where $\Delta$ is the time difference between node x and node y, and $\alpha$ is a parameter. The infection probability (e.g., the links between the nodes) can also be described as the weight of the influence between the nodes. The threshold estimation component 202 can calculate the infection probability equation. In other words, this infection probability equation expresses the probability at which node x (e.g., a person) infects node y (e.g., another person). The expression 1−Threshold(x) is the susceptibility of node x, where Threshold(x) is the threshold of node x. The susceptibility of node x (e.g., intrinsic risk of node x) can also be expressed as LR(x). The susceptibility of a node can also mean the weight of the influence from another node. The expression 1−Threshold(y) is the susceptibility of node y, where Threshold(y) is the threshold of node y. The susceptibility of node y (e.g., intrinsic risk of node y) can also be expressed as LR(y).

Let $f(x)=1-Threshold(x)$, $f(y)=1-Threshold(y)$, and the infection probability equation can be rewritten as $$e^{-\frac{\Delta}{\alpha}}$$

Using logistic regression, the infection probability equation can be rewritten as $$Pc(x, y) = \frac{1}{1 + e^{\beta x}} * e^{-\frac{\Delta}{\alpha}} * \frac{1}{1 + e^{\beta y}}.$$

Working with the log-likelihood function, the infection probability equation can be rewritten as log $$Pc(x, y) = \log\frac{1}{1 + e^{\beta x}} + \log e^{-\frac{\Delta}{\alpha}} + \log\frac{1}{1 + e^{\beta y}}.$$

In calculating the infection probability equation, the threshold estimation component 202 can use the gradient descent to solve the maximum likelihood estimation problem, thus, finding the infection probability. The gradient computation is similar to logistic regression. The maximum likelihood estimation is a general approach to estimating parameters in statistical models by maximizing the likelihood function. The gradient descent is an optimization algorithm, which can be used to find maximum (or minimum) of many different functions, including the likelihood function. The gradient descent is one way to learn the weight coefficients of a linear regression model.

Figure 3:
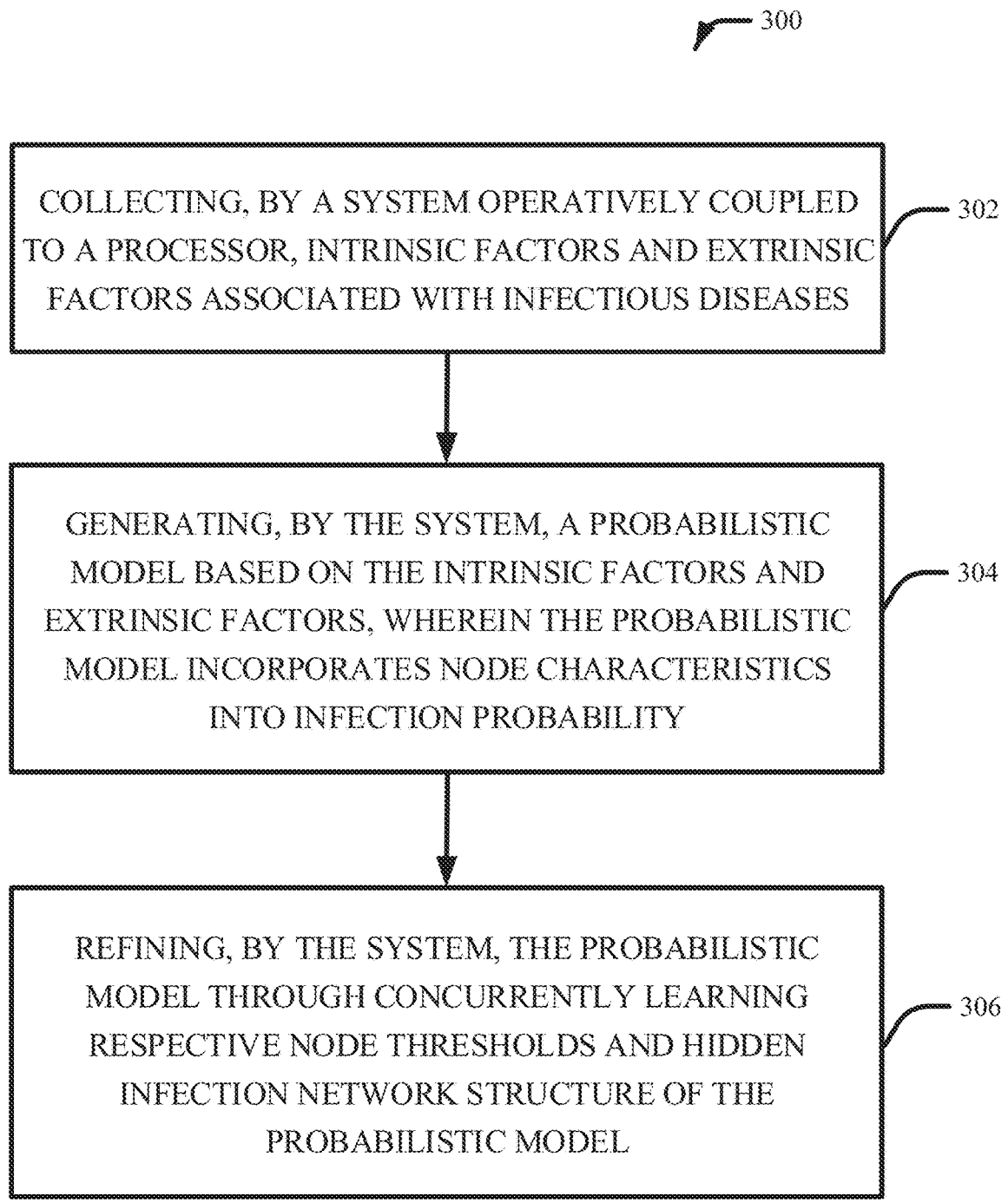
FIG. 3 illustrates a flow diagram of an example, non-limiting computer-implemented method facilitating predicting personalized risks based on intrinsic factors and extrinsic factors in accordance with one or more embodiments described herein.

FIG. 3 illustrates a flow diagram of an example, non-limiting computer-implemented method 300 facilitating predicting personalized risks based on intrinsic factors and extrinsic factors in accordance with one or more embodiments described herein. Repetitive description of like elements employed in other embodiments described herein is omitted for sake of brevity.

At 302, the computer-implemented method 300 can comprise collecting (e.g., via the collection component 108), by a system operatively coupled to a processor, the intrinsic factors and the extrinsic factors associated with infectious diseases. The intrinsic factors and the extrinsic factors can come from medical exams, medical records, past medical history, family medical history, health reports from government agencies, observational data, etc. At 304, the computer-implemented method 300 can comprise generating (e.g., via the construction component 110), by the system, a probabilistic model based on the intrinsic factors and the extrinsic factors, wherein the probabilistic model incorporates the node characteristics into the infection probability. At 306, the computer implemented method can comprise refining (e.g., the machine learning component 112), by the system, the model through concurrently learning the respective node thresholds and the hidden infection network structure of the probabilistic model.

Figure 4:
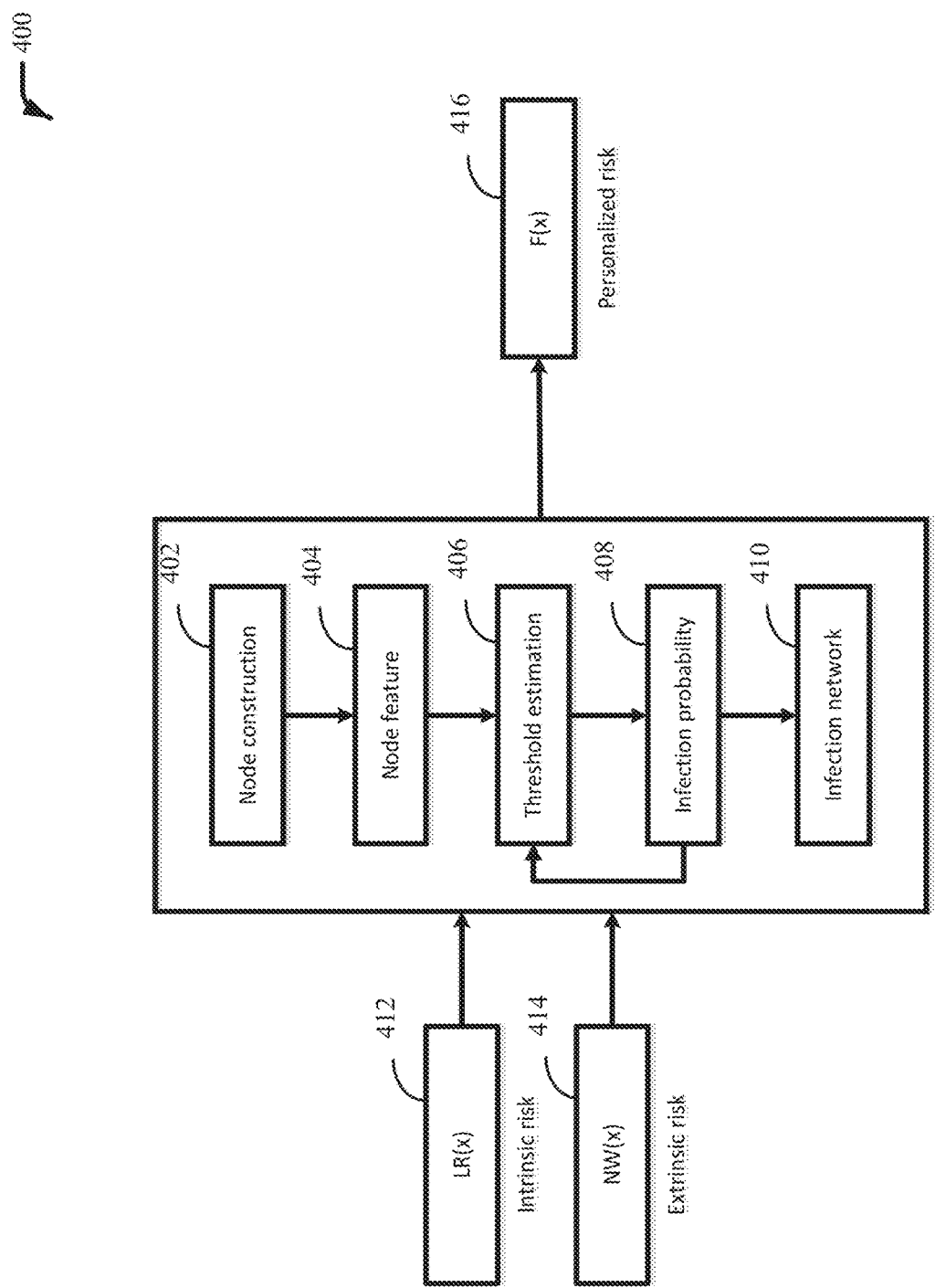
FIG. 4 illustrates a block diagram of an example, non-limiting methodology facilitating learning threshold and network structure simultaneously in accordance with one or more embodiments described herein.

FIG. 4 illustrates a block diagram of an example, non-limiting methodology 400 facilitating learning threshold and network structure simultaneously in accordance with one or more embodiments described herein. Repetitive description of like elements employed in other embodiments described herein is omitted for sake of brevity.

The node construction 402 can collect (e.g., via the collection component 108) extrinsic factors (e.g., time of infection, interactions, etc.) and can construct (e.g., via the construction component 110) the nodes. The node feature 404 can collect (e.g., via the collection component 108) the intrinsic factors (e.g., node characteristics such as age, weight, height, etc.) and incorporate (e.g., via the construction component 110) the intrinsic factors into the nodes. The threshold estimation 406 can use the intrinsic factor to calculate (e.g., via the threshold estimation component 202) the threshold of the nodes which can be a function of the node characteristics such as age, weight, height, etc. Based on the thresholds of the nodes, the estimation component 202 can also calculate the infection probability of the nodes (e.g., the patients, persons, etc.) using the infection probability equation. The infection probability equation can calculate the probability at which node x (e.g., a person) can infect node y (e.g., another person).

The infection network 410 can learn (e.g., via the machine learning component 112) the infection network structure. The infection network 410 can analyze (e.g., via the machine learning component) when a node (e.g., a person) infect another node (e.g., another person) to learn the infection network structure. Simultaneously while learning the infection network structure, the intrinsic risk 412 can also learn (e.g., via the machine learning component 112) the intrinsic risk (e.g., LR(x)) of the node and the extrinsic risk 414 can also learn (e.g., via the machine learning component 112) the extrinsic risk (e.g., NW(x)) of the nodes. The intrinsic risk and the extrinsic risk can be used to calculate the risk of a node, which can be a function of the intrinsic risk and the extrinsic risk. The personalized risk 416 can utilize the equation $F(x)=\pi*LR(x)+(1-)*NW(x)$ to calculate (e.g., via the machine learning component 112) the risk of the node (e.g., personalized risk, risk of the person, etc.).

Figure 5:
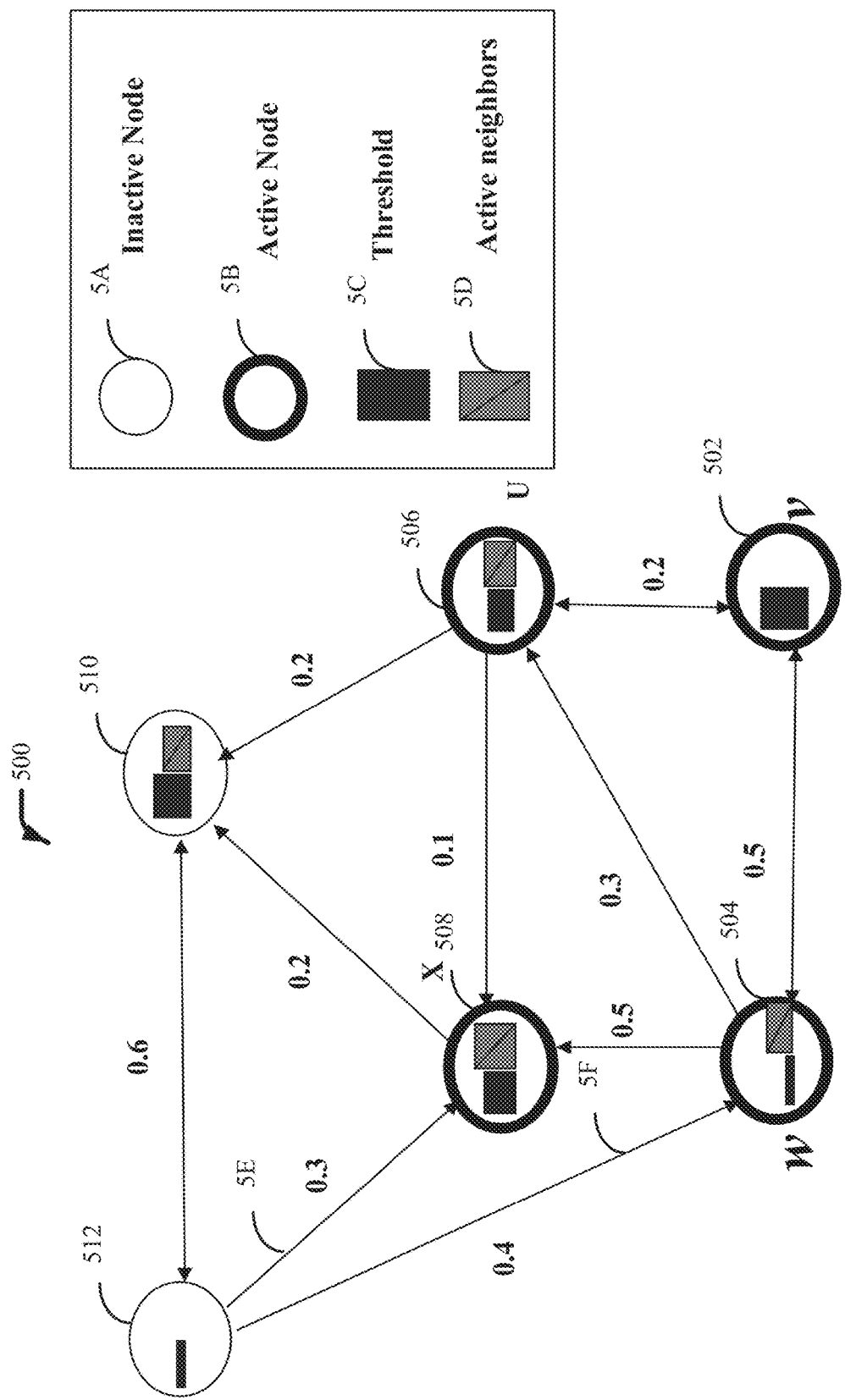
FIG. 5 illustrates a block diagram of an example, non-limiting linear threshold model facilitating predicting personalized risks based on intrinsic factors and extrinsic factors in accordance with one or more embodiments described herein.

FIG. 5 illustrates a block diagram of an example, non-limiting linear threshold model 500 facilitating predicting personalized risks based on intrinsic factors and extrinsic factors in accordance with one or more embodiments described herein. Repetitive description of like elements employed in other embodiments described herein is omitted for sake of brevity.

In a linear threshold model, a node v (e.g., a starting node) has random threshold $\theta_v \sim U[0,1]$. A node v can be influenced by neighbor w according to a weight $b_{vw}$ such that $$\sum_{w \text{ neighbor of } v} b_{v,w} \leq 1.$$

A node v becomes active when at least (weighted) $\theta_v$ fraction of its neighbors are active $$\sum_{w \text{ active neighbor of } v} b_{v,w} \geq \theta_v.$$

In the example linear threshold model 500, the nodes with the circle 5A indicates that the node is an inactive node. The nodes with the circle 5B indicates that the node is an active node. The box 5C illustrates the threshold, which can be compared to the strength of the active neighbors as indicated by box 5D. The threshold can be an indicator of the intrinsic factors such as age, weight, height, etc. The active neighbors are indicators of extrinsic factors such as influence of others. The links (e.g., arrows) can represent the probability of infection. For example, the node 502 may influence the node 506 with a probability of 0.2.

As illustrated in FIG. 5, node 502 is an active node or an infected node. Based on the definition of monotonicity, active nodes never deactivate or becomes uninfected. Active nodes can cause other nodes to activate or become infected. As illustrated in FIG. 5, node 502 activated or infected node 504. Inside the node 504 are two boxes that symbolizes box 5C and box 5D. The box 5D inside the node 504 is bigger than the box 5C inside the node 504, which indicates that the influence of others (e.g., infection from the node 502) is stronger than the threshold of the node 504. The threshold of the node 504 is not strong enough to fight off the infection from the node 502, and the node 504 becomes infected. The node 504 then passes the infection on to the node 506. The active neighbors box 5D in the node 506 is slightly stronger than the threshold, therefore, the node 506 also becomes infected. The node 506 then passes the infection on to the node 508. The active neighbors box 5D in the node 508 is stronger than the threshold, therefore, the node 508 also becomes infected. The node 508 then interacts with the node 510. However, as illustrated, the threshold inside the node 510 is stronger than the influence from node 508. Therefore, the node 510 remains inactive. The node 510 does not activate the node 512 because the node 510 is inactive. Based on the directions of the arrow 5E and 5F, the nodes 508 and 504, respectively, do not interact with the node 512. Therefore, the node 512 remains inactive.

The linear threshold model 500 illustrates how one node (e.g., person) can become infected while another node (e.g., another person) remains uninfected. Based on the intrinsic characteristics of a person, one person may be able to fight off an infectious disease better than another person. The intrinsic characteristics can be a person's age, weight, height, etc. For example, a fit person with a good immune system is going to be able to fight off infections better than someone who is overweight and has a weakened immune system.

FIGS. 6 through 12 illustrate block diagrams of an example, non-limiting independent cascade model 600 facilitating predicting personalized risks based on intrinsic factors and extrinsic factors in accordance with one or more embodiments described herein. Repetitive description of like elements employed in other embodiments described herein is omitted for sake of brevity. In an independent cascade model, when node v (e.g. the starting node) becomes active, it has a single chance of activating a currently inactive neighbor w. The activation attempt succeeds with probability $p_{vw}$. Links can connect a node to another node to demonstrate interactions between the nodes.

Arrows indicate the direction of infection. A probability of infection can be associated with the links to show the probability of one node infecting another node, which can be calculated based on the infection probability equation. If the infection probability value of the active neighbors is bigger than the threshold of a node, the node will become active. This means the attempt is a successful attempt, otherwise, it is an unsuccessful attempt.

As illustrated in FIGS. 6 through 12, the circle 6A indicates that a node is an inactive node (e.g., not infected). The circle 6B indicates that a node is an active node (e.g., infected). The circle 6C indicates that a node is a newly active node (e.g., newly infected). The arrow 6D (e.g., successful attempt 6D) indicates that the attempt to activate a neighboring node is a successful attempt. The arrow 6E (e.g., unsuccessful attempt 6E) indicates that the attempt to activate a neighboring node is an unsuccessful attempt. The arrows 6D and 6E are directions of the disease propagation from an active node to an inactive node.

Figure 6:
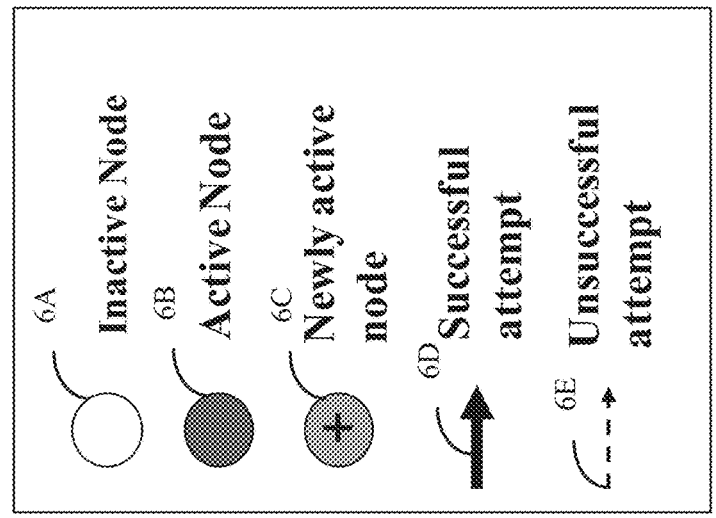
FIGS. 6 through 12 illustrate block diagrams of an example, non-limiting independent cascade model facilitating predicting personalized risks based on intrinsic factors and extrinsic factors in accordance with one or more embodiments described herein.
Figure 6:
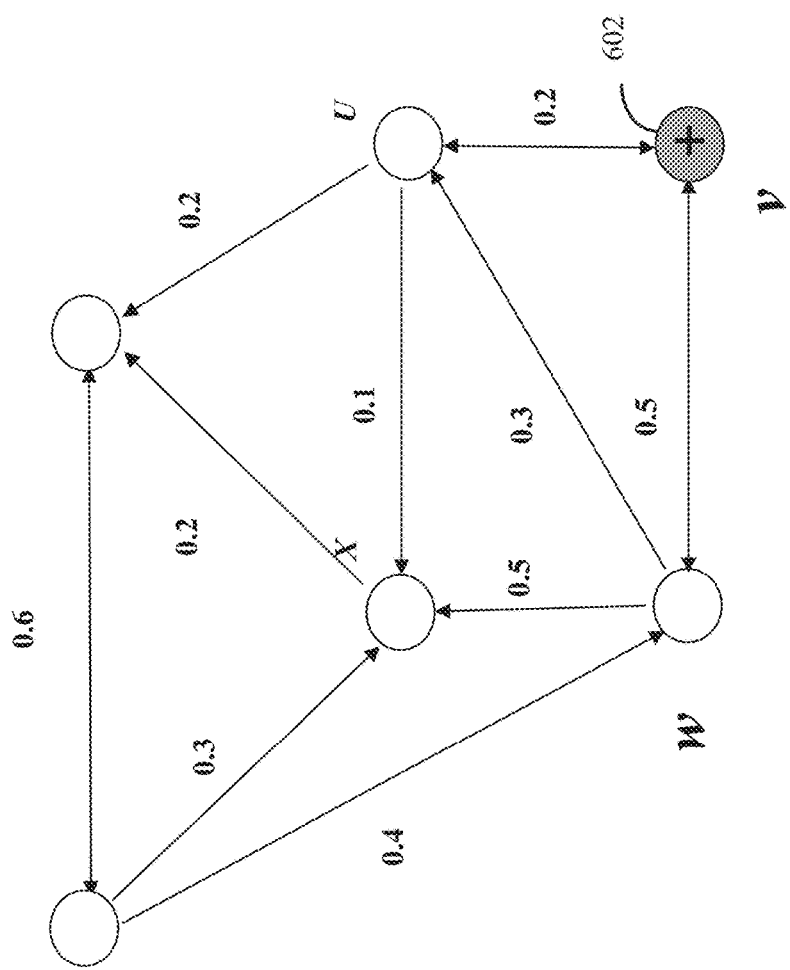

In FIG. 6, the node 602 is a newly active node, and the only active node. The node 602 is the first got become active or infected. All the other nodes are inactive nodes. The other inactive nodes have yet to come in to contact with an active node. The arrows between the nodes shows how the nodes are linked. However, there are no attempts from node 602 to activate (e.g., infect) another node as can be depicted by the arrows 6D and 6E.

Figure 7:
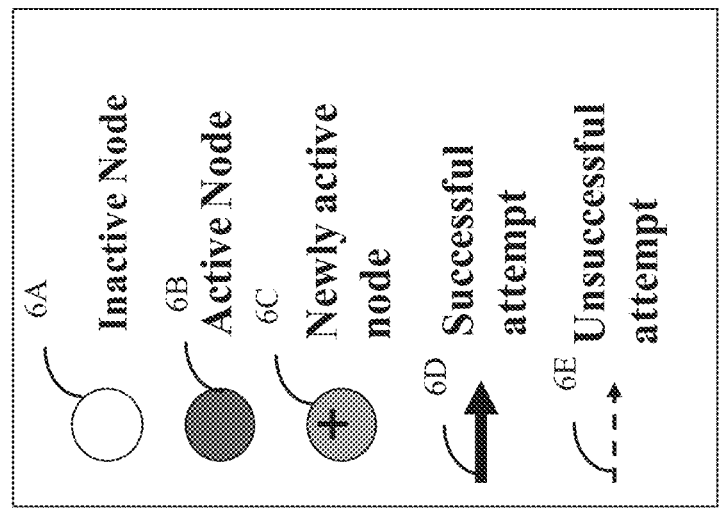
Figure 7:
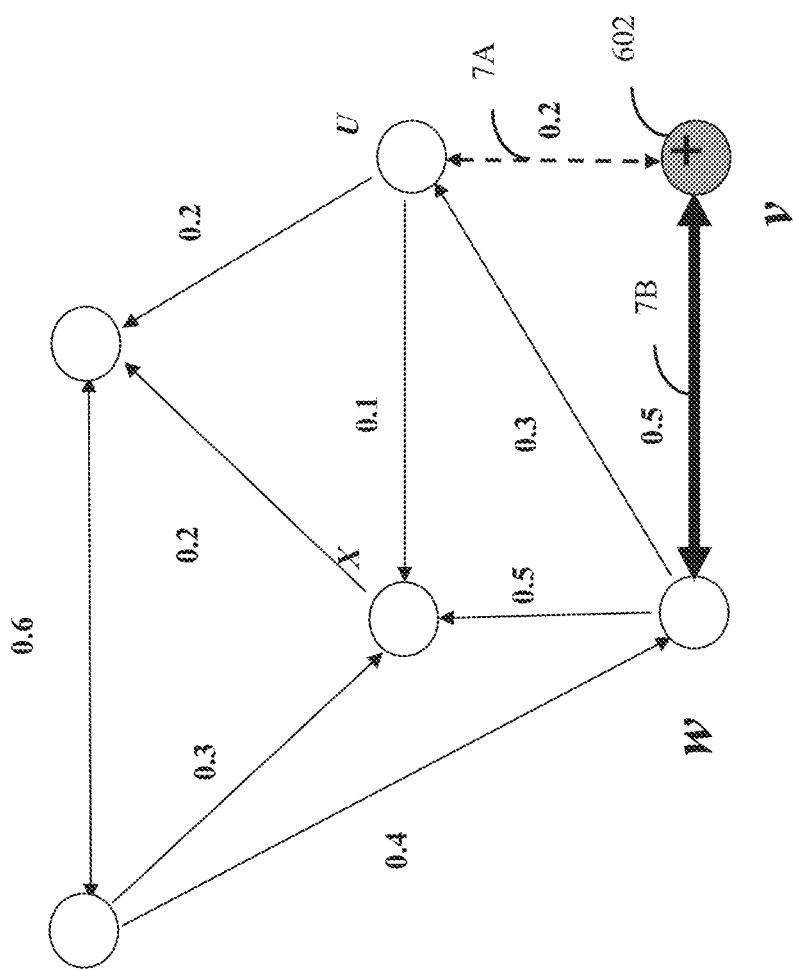

FIG. 7 illustrates that the node 602 has an unsuccessful attempt 7A and a successful attempt 7B. The unsuccessful attempt 7A has an infection probability of 0.2. That means the probability of node 602 activating (e.g., infecting) the node it is adjacent to and connect to is 0.2. The node 602 also a successful attempt 7B with an infection probability of 0.5. The infection probability value 0.5 is enough to active the adjacent node as illustrated in the next figure.

Figure 8:
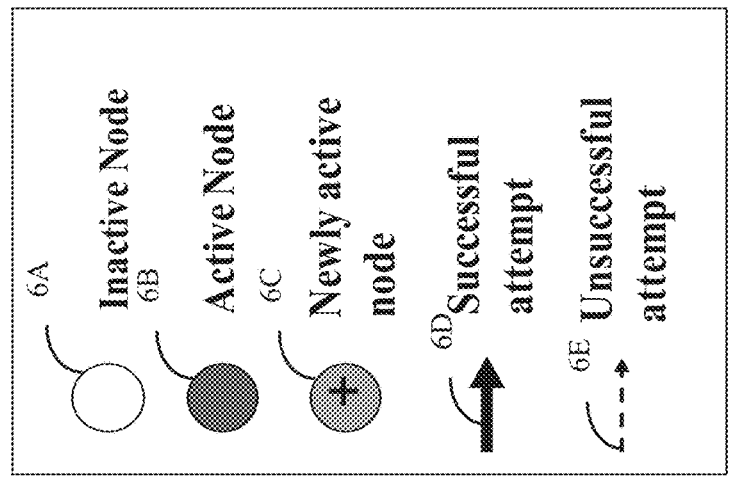
Figure 8:
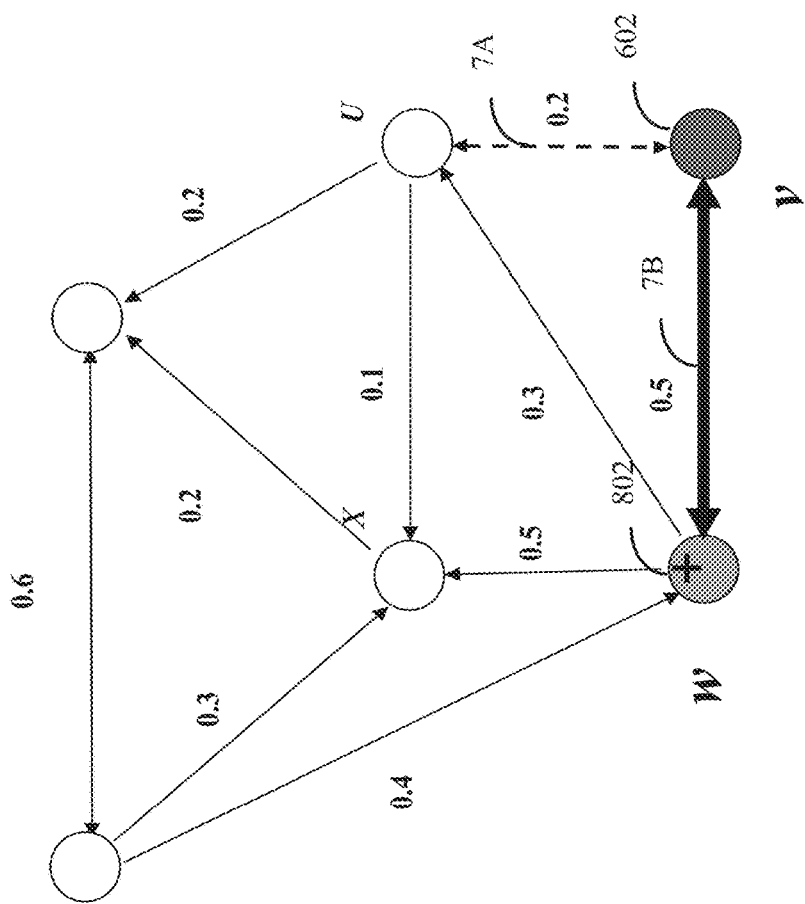

FIG. 8 illustrates that the successful attempt 7B (e.g., arrow 7B) activated the node 802 and changed the node 802 into a newly active node. The arrow 7B shows interaction between the node 602 and the node 802. The arrow 7B has as an infection probability a value of 0.5, which is enough to activate node 802. The node 602 is still an active node but no longer a newly active node. The node 602 is now an active node. A node that is active cannot be deactivate. This is called monotonicity. The newly active node 802 can now attempt to activate other inactive nodes as illustrated in the next figure.

Figure 9:
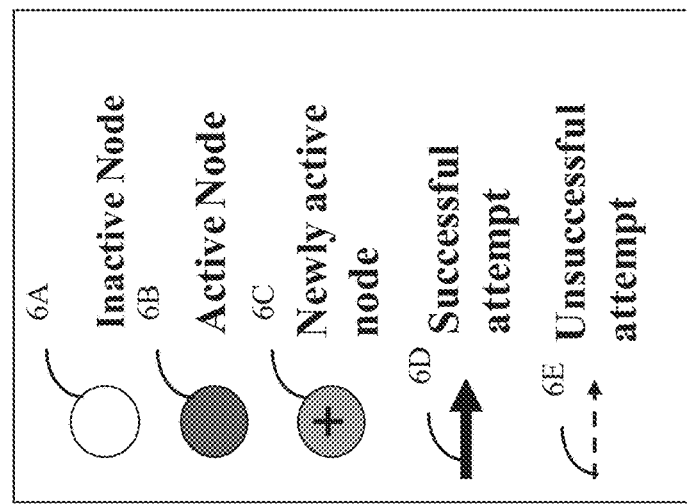
Figure 9:
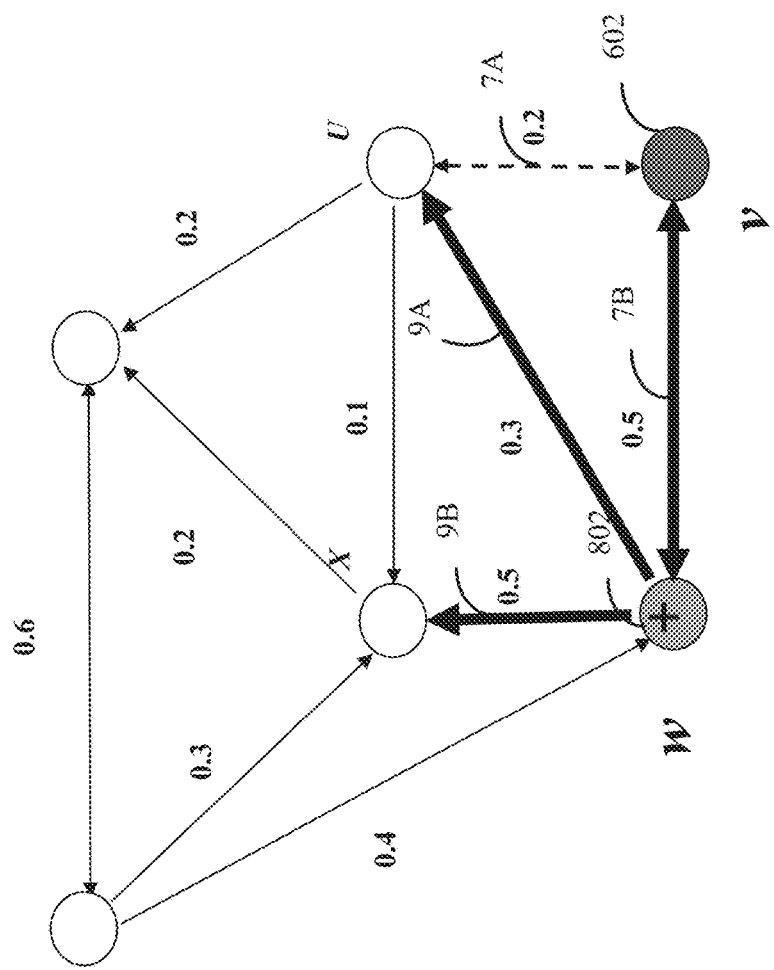
Figure 10:
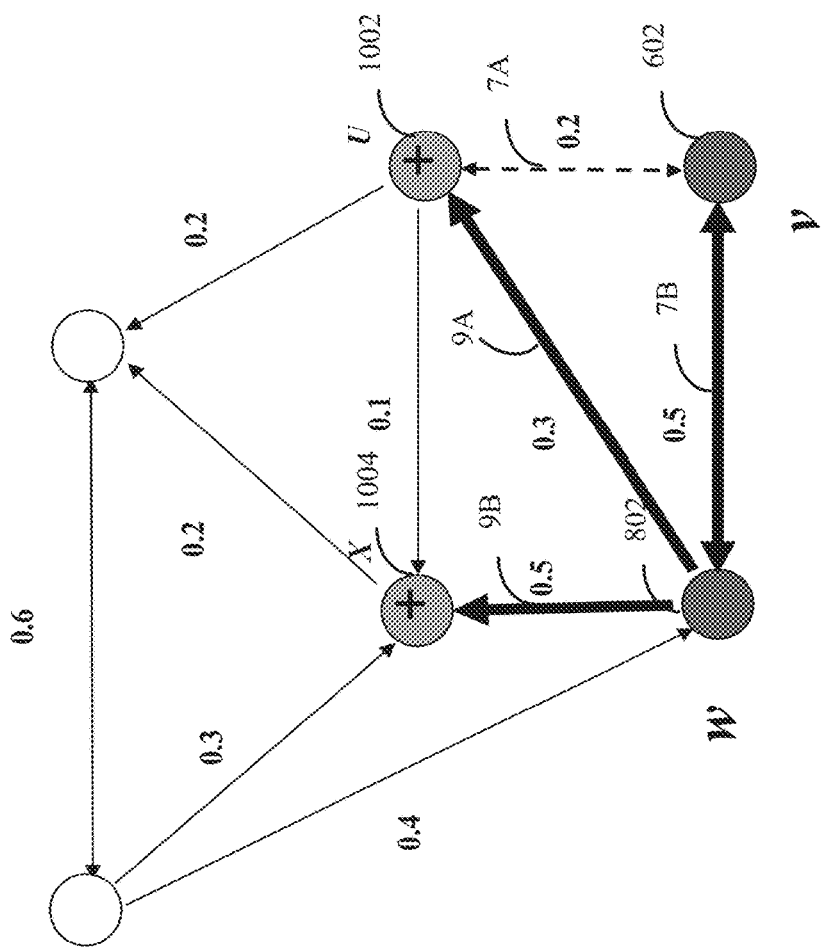

FIG. 9 illustrates that node 802 has two successful attempts, the successful attempt 9A and the successful attempt 9B. The successful attempt 9A has an infection probability of 0.3. The infection probability of 0.3 is enough for the node 802 to activate the node it is connected to as shown in FIG. 10. The successful attempt 9B has an infection probability 0.5. The infection probability of 0.5 is enough for the node 802 to activate the node it is connected to as shown in FIG. 10.

FIG. 10 illustrates the node 802 successfully activated the newly active node 1002 and the newly active node 1004. With an infection probability of 0.3 between the node 802 and the node 1002, the node 802 successfully activated the node 1002. With an infection probability of 0.5 between the node 802 and the node 1004, the node 802 successfully activated the node 1004. The node 802, once a newly active node, is now an active node. The node 1002 and the node 1004 are now newly active nodes that can attempt to activate other inactive nodes as shown in FIG. 11.

Figure 11:
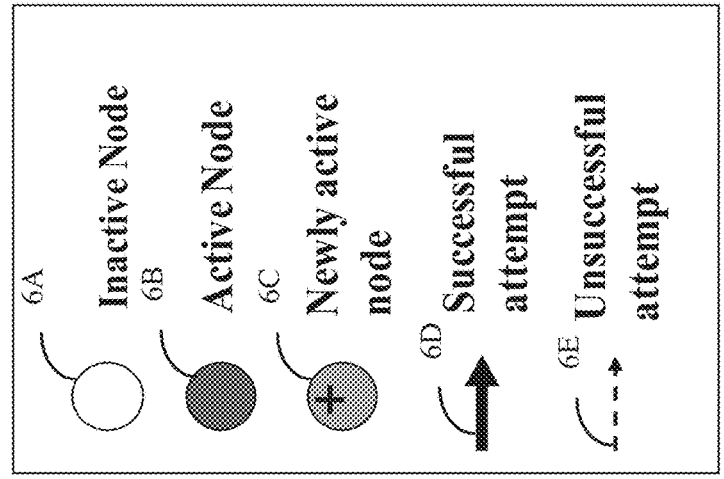
Figure 11:
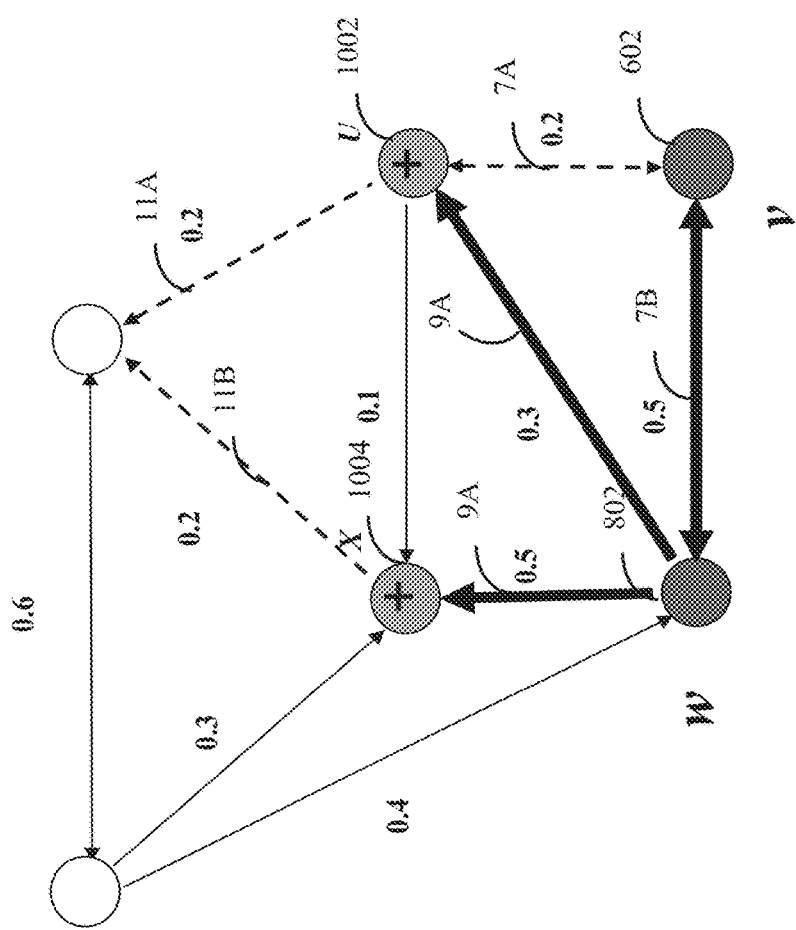

FIG. 11 illustrates that the nodes 1002 and 1004 have unsuccessful attempts 11A and 11B, respectively. The unsuccessful attempt 11A by the node 1002 has an infection probability value of 0.2. Likewise, the unsuccessful attempt 11B by the node 1004 also has an infection probability value of 0.2. This means that neither the node 1002 nor the node 1004 will be successful in activating the node that the arrows 11A and 11B are pointed to as shown in the next figure, FIG. 12.

Figure 12:
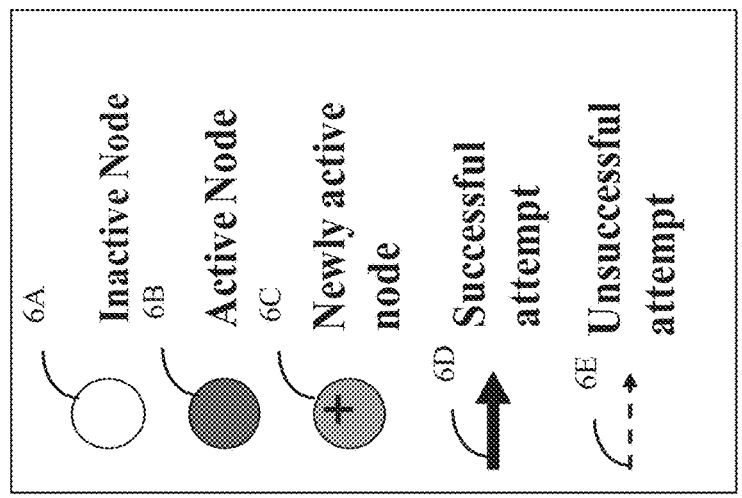
Figure 12:
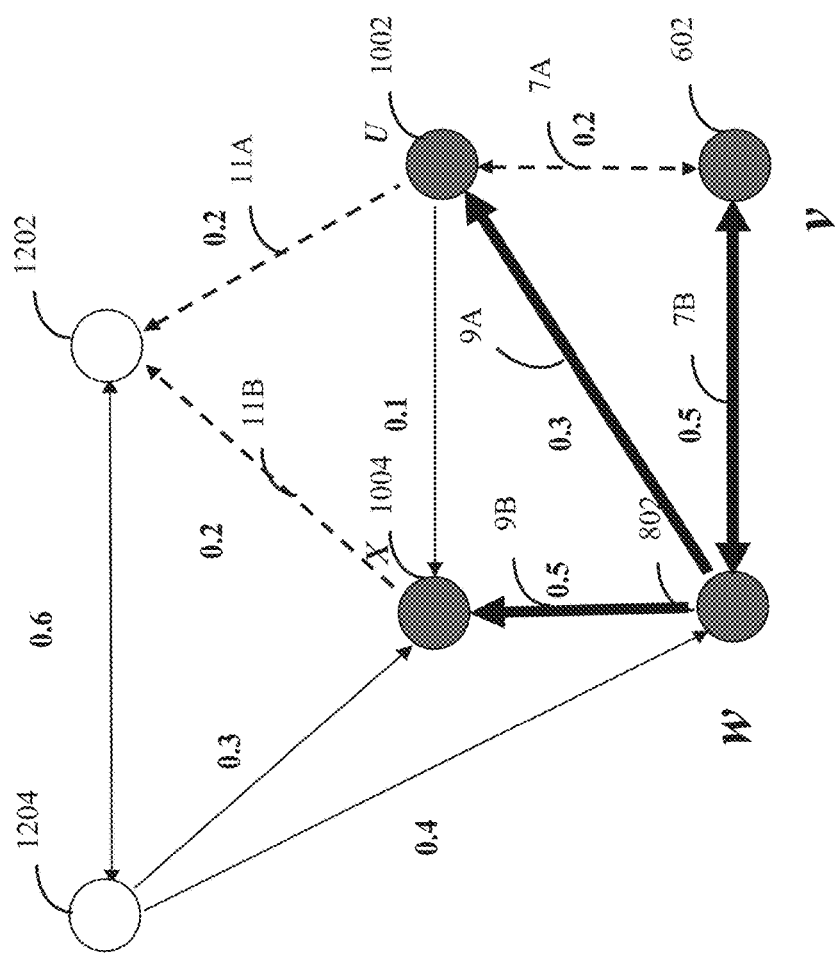

FIG. 12 illustrates that the node 1002 and the node 1004 are unable to activate the node 1202 through the unsuccessful attempt 11A and the unsuccessful attempt 11B. Therefore, the node 1202 remains inactive. The inactive node 1202 cannot attempt to activate the node 1204 because the node 1202 is inactive. An active node can cause other inactive nodes to become active, but an inactive node cannot. The infection probabilities associated with the links are just for illustration. In this example, the infection probability value of 0.6 between the node 1202 and the node 1204 is just for illustration. Whether a node becomes active or not depends on the value of the threshold and the active neighbors. The node 1202 (e.g., node 510 in FIG. 5) is not infected because the value of active neighbors is smaller than the value of the threshold. As node 1202 is inactive, the node 1204 cannot be infected. There are no attempts from any other nodes to activate the node 1204, and so the node 1204 also remains inactive. The nodes 602, 802, 1002 and 1004 all remain as active nodes. There are no newly active nodes.

From the independent cascade model 600, the hidden network structure of user interaction can be inferred. The data for the independent cascade model 600 can be observed or received from a stored health databased. For example, a governmental agency may have an interest in storing infection data. An independent cascade model such as the independent cascade model 600 can be constructed to infer user interaction. The arrows on the independent cascade model 600 can show the direction of the disease propagation or the inferred user interaction. The numbers along the arrows can indicate the probability of infection for the nodes between the links (e.g. arrows, propagation, etc.). For example, FIG. 8 illustrates that the 602 has an unsuccessful attempt 7A which has a probability of 0.2, thus, it could not cause an infection in that disease propagation direction. The node 602 also has a successful attempt 7B which has a probability of 0.5, thus, it successfully infected the node 802.

The threshold of the nodes and the structure of the infection network can be learned simultaneously via the machine learning component 112. The threshold estimation component 202 can calculate the infection probability of the links. The process can be performed iteratively to refine the models and achieve the best infection network structure and threshold that maximizes the threshold of all the cascade.

Figure 13:
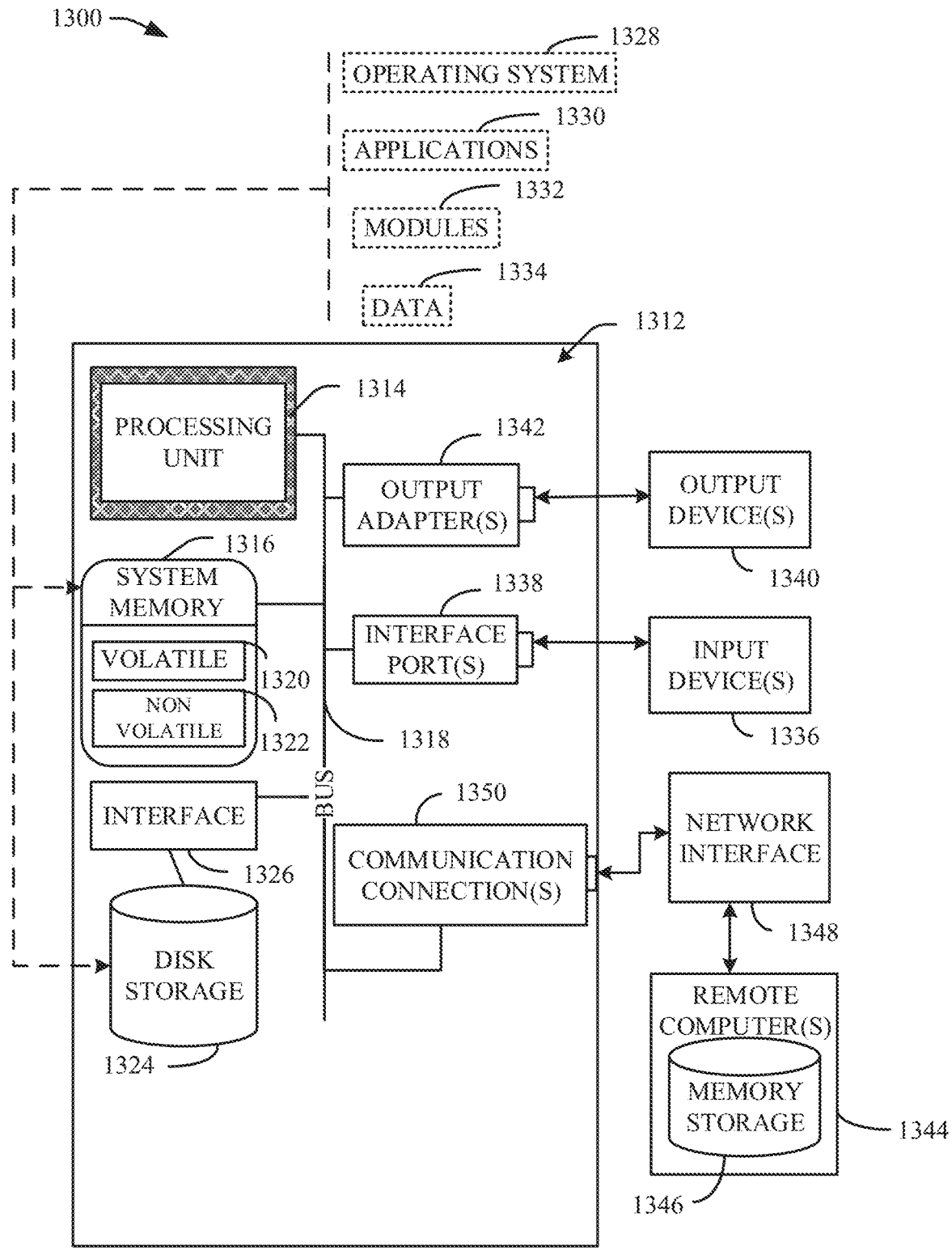
FIG. 13 illustrates a block diagram of an example, non-limiting operating environment in which one or more embodiments described herein can be facilitated.

In order to provide a context for the various aspects of the disclosed subject matter, FIG. 13 as well as the following discussion are intended to provide a general description of a suitable environment in which the various aspects of the disclosed subject matter can be implemented. FIG. 13 illustrates a block diagram of an example, non-limiting operating environment in which one or more embodiments described herein can be facilitated. Repetitive description of like elements employed in other embodiments described herein is omitted for sake of brevity.

With reference to FIG. 13, a suitable operating environment 1300 for implementing various aspects of this disclosure can also include a computer 1312. The computer 1312 can also include a processing unit 1314, a system memory 1316, and a system bus 1318. The system bus 1318 couples system components including, but not limited to, the system memory 1316 to the processing unit 1314. The processing unit 1314 can be any of various available processors. Dual microprocessors and other multiprocessor architectures also can be employed as the processing unit 1314. The system bus 1318 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1316 can also include volatile memory 1320 and nonvolatile memory 1322. The basic input/output system (BIOS), containing the basic routines to transfer information between elements within the computer 1312, such as during start-up, is stored in nonvolatile memory 1322. Computer 1312 can also include removable/non-removable, volatile/non-volatile computer storage media. FIG. 13 illustrates, for example, a disk storage 1324. Disk storage 1324 can also include, but is not limited to, devices like a magnetic disk drive, floppy disk drive, tape drive, Jaz drive, Zip drive, LS-100 drive, flash memory card, or memory stick. The disk storage 1324 also can include storage media separately or in combination with other storage media. To facilitate connection of the disk storage 1324 to the system bus 1318, a removable or non-removable interface is typically used, such as interface 1326. FIG. 13 also depicts software that acts as an intermediary between users and the basic computer resources described in the suitable operating environment 1300. Such software can also include, for example, an operating system 1328. Operating system 1328, which can be stored on disk storage 1324, acts to control and allocate resources of the computer 1312.

System applications 1330 take advantage of the management of resources by operating system 1328 through program modules 1332 and program data 1334, e.g., stored either in system memory 1316 or on disk storage 1324. It is to be appreciated that this disclosure can be implemented with various operating systems or combinations of operating systems. A user enters commands or information into the computer 1312 through input device(s) 1336. Input devices 1336 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1314 through the system bus 1318 via interface port(s) 1338. Interface port(s) 1338 include, for example, a serial port, a parallel port, a game port, and a universal serial bus (USB). Output device(s) 1340 use some of the same type of ports as input device(s) 1336. Thus, for example, a USB port can be used to provide input to computer 1312, and to output information from computer 1312 to an output device 1340. Output adapter 1342 is provided to illustrate that there are some output devices 1340 like monitors, speakers, and printers, among other output devices 1340, which require special adapters. The output adapters 1342 include, by way of illustration and not limitation, video and sound cards that provide a means of connection between the output device 1340 and the system bus 1318. It should be noted that other devices and/or systems of devices provide both input and output capabilities such as remote computer(s) 1344.

Computer 1312 can operate in a networked environment using logical connections to one or more remote computers, such as remote computer(s) 1344. The remote computer(s) 1344 can be a computer, a server, a router, a network PC, a workstation, a microprocessor based appliance, a peer device or other common network node and the like, and typically can also include many or all of the elements described relative to computer 1312. For purposes of brevity, only a memory storage device 1346 is illustrated with remote computer(s) 1344. Remote computer(s) 1344 is logically connected to computer 1312 through a network interface 1348 and then physically connected via communication connection 1350. Network interface 1348 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1350 refers to the hardware/software employed to connect the network interface 1348 to the system bus 1318. While communication connection 1350 is shown for illustrative clarity inside computer 1312, it can also be external to computer 1312. The hardware/software for connection to the network interface 1348 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc., that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system, comprising:
 a memory that stores computer executable components;
 a processor, operably coupled to the memory, and that executes computer executable components stored in the memory, wherein the computer executable components comprise:
  a collection component that collects intrinsic factors and extrinsic factors associated with infectious diseases and persons;
  a construction component that generates a probabilistic model for determining infection probabilities of the persons based on the intrinsic factors and extrinsic factors, wherein nodes of the probabilistic model respectively represent the persons, and the probabilistic model incorporates node characteristics of the persons into determining the infection probabilities; and
  a machine learning component that:
   refines the probabilistic model through concurrently learning respective node thresholds of the nodes and hidden infection network structure of the probabilistic model resulting in a trained probabilistic model, wherein the respective node thresholds represent susceptibilities of the persons to the infectious diseases, and the hidden infection network structure comprises connections between the nodes representing interactions between the persons; and wherein:
the collection component collects additional intrinsic factors and additional extrinsic factor associated with a specified person, and
the machine learning component:
determines, using the trained probabilistic model, an infection probability for the specified person to become infected by an infectious disease of the infection diseases after exposure to one or more persons infected with the infectious disease, and
informs the specified person of the infection probability in association with clinical decision making regarding one or more treatments.

2. The system of claim 1, further comprising a threshold estimation component that estimates the respective node thresholds of the nodes within the probabilistic model and calculates the infection probability based on the respective node thresholds.

3. The system of claim 2, wherein the infection probability Pc(x,y) of node y being infected node x with the infectious disease is represented by:

$$Pc(x, y) = (1 - \text{Threshold}(x)) * e^{-\frac{\Delta}{\alpha}} * (1 - \text{Threshold}(y)),$$

where 1−Threshold(x) is the susceptibility of node x, 1−Threshold(y) is the susceptibility of node y, and $$e^{-\frac{\Delta}{\alpha}}$$

is an exponential model where $\Delta$ is the time difference between node x and node y being infected with the infection disease, and $\alpha$ is a parameter of the infectious disease.

4. The system of claim 3, wherein a personalized risk F(x) of node x as a function of intrinsic risk and extrinsic risk is represented by:

$$F(x)=\pi*LR(x)+(1-\pi)*NW(x), \text{ wherein:}$$

LR(x) is the intrinsic risk and is represented by 1−Threshold(x);
NW(x) is the extrinsic risk; and
$\pi$ is a parameter that controls the respective importance of LR(x) and (NW(x)).

5. The system of claim 2, wherein a property of the infectious disease is factored in calculating the infection probability.

6. The system of claim 1, wherein the machine learning component calculates an intrinsic risk of the person and an extrinsic risk of the person based on individual characteristics of the person and interactions of the person.

7. The system of claim 6, wherein the machine learning component calculates a personalized risk of the person as a function of the intrinsic risk and the extrinsic risk.

8. A computer-implemented method, comprising:
collecting, by a system operatively coupled to a processor, intrinsic factors and extrinsic factors associated with infectious diseases and persons;
generating, by the system, a probabilistic model for determining infection probabilities of the persons based on the intrinsic factors and extrinsic factors, wherein nodes of the probabilistic model respectively represent the persons, and the probabilistic model incorporates node characteristics of the persons into determining the infection probabilities;
refining, by the system, the probabilistic model through concurrently learning respective node thresholds and hidden infection network structure of the probabilistic model resulting in a trained probabilistic model, wherein the respective node thresholds represent susceptibilities of the persons to the infectious diseases, and the hidden infection network structure comprises connections between the nodes representing interactions between the persons;
collecting, by the system, additional intrinsic factors and additional extrinsic factor associated with a specified person;
determining, by the system, using the trained probabilistic model, an infection probability for the specified person to become infected by an infectious disease of the infection diseases after exposure to one or more persons infected with the infectious disease; and
informing, by the system, the specified person of the infection probability in association with clinical decision making regarding one or more treatments.

9. The computer-implemented method of claim 8, further comprising estimating the respective node thresholds of the nodes within the probabilistic models and calculates the infection probability based on the respective node thresholds.

10. The computer-implemented method of claim 9, wherein the infection probability Pc(x,y) of node y being infected node x with the infectious disease is represented by:

$$Pc(x, y) = (1 - \text{Threshold}(x)) * e^{-\frac{\Delta}{\alpha}} * (1 - \text{Threshold}(y)),$$

where 1−Threshold(x) is the susceptibility of node x, 1−Threshold(y) is the susceptibility of node y, and $$e^{-\frac{\Delta}{\alpha}}$$

is an exponential model where $\Delta$ is the time difference between node x and node y being infected with the infection disease, and $\alpha$ is a parameter of the infectious disease.

11. The computer-implemented method of claim 10, wherein a personalized risk F(x) of node x as a function of intrinsic risk and extrinsic risk is represented by:

$$F(x)=\pi*LR(x)+(1-\pi)*NW(x), \text{ wherein:}$$

LR(x) is the intrinsic risk and is represented by 1−Threshold(x);
NW(x) is the extrinsic risk; and
$\pi$ is a parameter that controls the respective importance of LR(x) and (NW(x)).

12. The computer-implemented method of claim 9, wherein the infectious disease is factored in calculating the infection probability.

13. The computer-implemented method of claim 11, further comprising calculating an intrinsic risk of the person and an extrinsic risk of the person based on individual characteristics of the person and interactions of the person.

14. The computer-implemented method of claim 13, further comprising calculating a personalized risk of the person as a function of the intrinsic risk and the extrinsic risk.

15. A computer program product that facilitates predicting personalized risks based on intrinsic factors and extrinsic factors, the computer program product comprising a computer readable storage medium having program instructions embodied therewith, the program instructions executable by a processor to cause the processor to:
collect the intrinsic factors and the extrinsic factors associated with infectious diseases and persons;
generate a probabilistic model for determining infection probabilities of the persons based on the intrinsic factors and extrinsic factors, wherein nodes of the probabilistic model respectively represent the persons, and the probabilistic model incorporates node characteristics of the persons into determining the infection probabilities;
refine the probabilistic model through concurrently learning respective node thresholds and hidden infection network structure of the probabilistic model resulting in a trained probabilistic model, wherein the respective node thresholds represent susceptibilities of the persons to the infectious diseases, and the hidden infection network structure comprises connections between the nodes representing interactions between the persons;
collect additional intrinsic factors and additional extrinsic factor associated with a specified person;
determine, using the trained probabilistic model, an infection probability the specified person to become infected by an infectious disease of the infection diseases after exposure to one or more persons infected with the infectious disease; and
inform the specified person of the infection probability in association with clinical decision making regarding one or more treatments.

16. The computer program product of claim 15, wherein the program instructions are further executable to cause the processor to:
estimate the respective node thresholds of the nodes within the probabilistic model and calculate the infection probability based on the respective node thresholds.

17. The computer program product of claim 16, wherein the infection probability Pc(x,y) of node y being infected node x with the infectious disease is represented by:

$$Pc(x, y) = (1 - \text{Threshold}(x)) * e^{-\frac{\Delta}{\alpha}} * (1 - \text{Threshold}(y)),$$

where 1−Threshold(x) is the susceptibility of node x, 1−Threshold(y) is the susceptibility of node y, and $$e^{-\frac{\Delta}{\alpha}}$$

is an exponential model where $\Delta$ is the time difference between node x and node y being infected with the infection disease, and $\alpha$ is a parameter of the infectious disease.

18. The computer program product of claim 17, wherein a personalized risk F(x) of node x as a function of intrinsic risk and extrinsic risk is represented by:

$$F(x)=\pi*LR(x)+(1-\pi)*NW(x), \text{ wherein:}$$

LR(x) is the intrinsic risk and is represented by 1−Threshold(x);
NW(x) is the extrinsic risk; and
$\pi$ is a parameter that controls the respective importance of LR(x) and (NW(x)).

19. The computer program product of claim 15, wherein the program instructions are further executable to cause the processor to:
calculate an intrinsic risk of the person and an extrinsic risk of the person based on individual characteristics of the person and interactions of the person.

20. The computer program product of claim 19, wherein the program instructions are further executable to cause the processor to:
calculate a personalized risk of the person as a function of the intrinsic risk and the extrinsic risk.

* * * * *